(12) United States Patent
Kim

(10) Patent No.: US 7,879,092 B2
(45) Date of Patent: Feb. 1, 2011

(54) DENTAL IMPLANT COATED WITH RECOMBINANT BONE MORPHOGENIC PROTEIN

(75) Inventor: Soo Hong Kim, 102-1302, SamikGreen Apt. 245-23, 35/3, Daeyeon-dong, Nam-gu, Busan (KR) 808-777

(73) Assignees: Cowellmedi Co., Ltd, Busan (KR); Soo Hong Kim, Busan (KR)

( * ) Notice: Subject to any disclaimer, the term of this patent is extended or adjusted under 35 U.S.C. 154(b) by 0 days.

(21) Appl. No.: 11/719,740

(22) PCT Filed: Oct. 19, 2006

(86) PCT No.: PCT/KR2006/004234

§ 371 (c)(1),
(2), (4) Date: May 18, 2007

(87) PCT Pub. No.: WO2007/074968

PCT Pub. Date: Jul. 5, 2007

(65) Prior Publication Data

US 2009/0155746 A1    Jun. 18, 2009

(30) Foreign Application Priority Data

Dec. 26, 2005   (KR) .................. 10-2005-0129577
Jun. 29, 2006   (KR) .................. 10-2006-0059457

(51) Int. Cl.
*A61F 2/02* (2006.01)
*A61F 2/28* (2006.01)
*A61F 2/70* (2006.01)
*A61C 13/00* (2006.01)
*A61C 8/00* (2006.01)

(52) U.S. Cl. ............ 623/11.11; 623/16.11; 623/17.17; 623/20.17; 623/25.53; 433/167; 433/173; 433/174

(58) Field of Classification Search .......... 623/16; 433/173, 174
See application file for complete search history.

(56) References Cited

U.S. PATENT DOCUMENTS 5,344,654 A * 9/1994 Rueger et al. ............... 424/423

* cited by examiner

*Primary Examiner*—Gary B. Nickol
*Assistant Examiner*—Sandra Wegert
(74) *Attorney, Agent, or Firm*—John K. Park; Park Law Firm

(57) ABSTRACT

The present invention relates to a dental implant having recombinant bone morphogenic protein coated on the processed surface thereof, which, when implanted into the jawbone, enables undifferentiated adult cells around the implant site to be rapidly differentiated into osteoblasts so as to induce osteoconductive healing to thereby reduce a healing period, as well as a coating method thereof. According to the invention, recombinant bone morphogenic protein BMP-2 penetrates between ceramic balls formed on the dental implant surface, sheet structures of calcium triphosphate or fine pores formed by anodic oxidation, so as to form a coating film. Thus, the recombinant bone morphogenic protein BMP-2 is not detached from the dental implant surface even during the surgical implantation of the implant. Also, because the recombinant bone morphogenic protein coated on the surface of the dental implant is primarily coated mainly on the deep valley of the implant surface, it can be prevented from being peeled due to mechanical friction during the surgical implantation of the implant. Also, because a minimum amount of the protein coated on the implant surface locally acts on tissue around the implant site, the protein has little or no side effects. In addition, the protein shows pharmacological effects to enable undifferentiated adult cells around the implant to be differentiated into osteoblasts so as to induce enhanced osteoconductive healing to thereby significantly reduce the osseointegration period of the implant.

2 Claims, 6 Drawing Sheets

[Fig. 1]
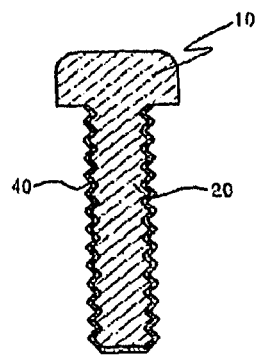
[Fig. 2]
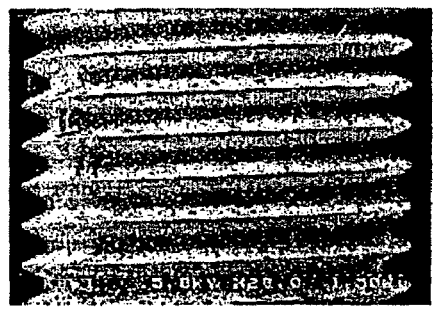
[Fig. 3]
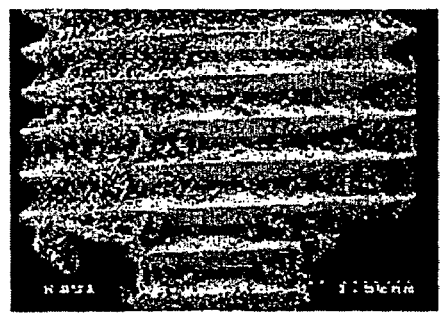
[Fig. 4]
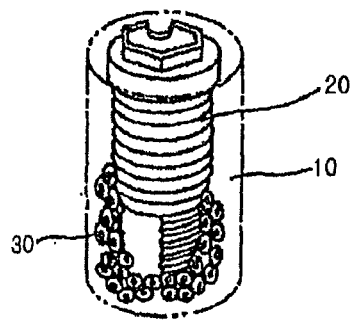

[Fig. 5]
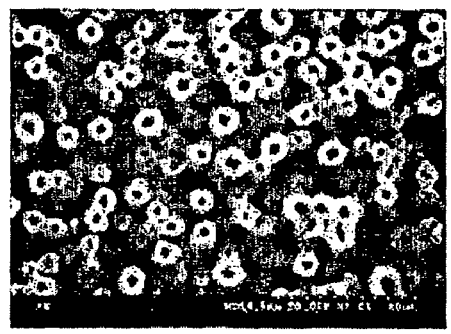
[Fig. 6]
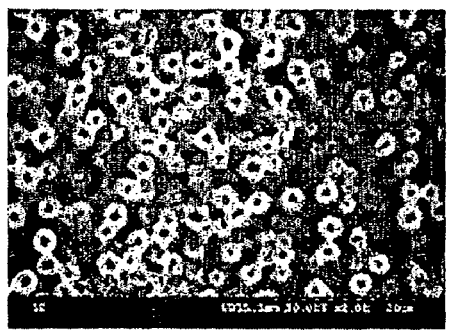
[Fig. 7]
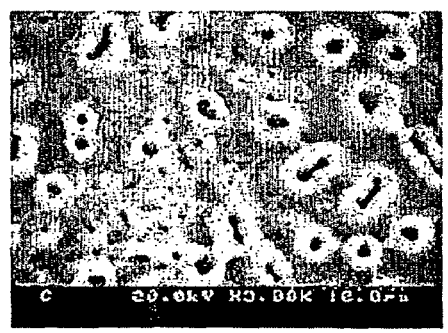
[Fig. 8]
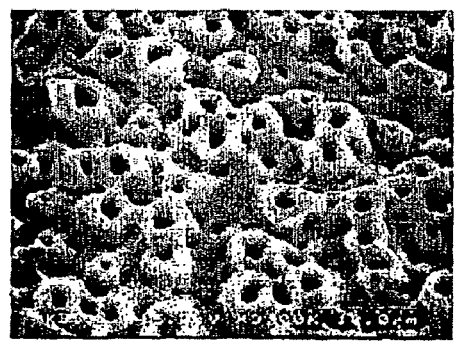

[Fig. 9]
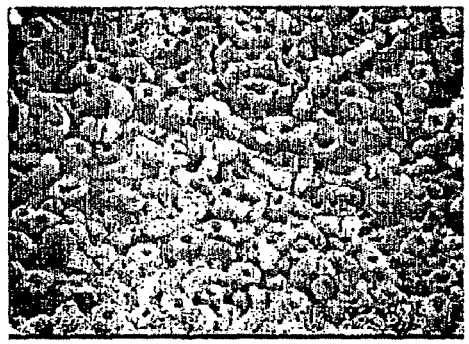
[Fig. 10]
[Fig. 11]
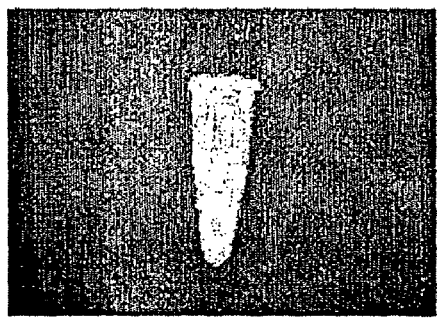
[Fig. 12]
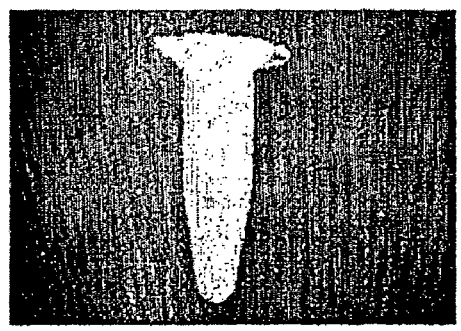

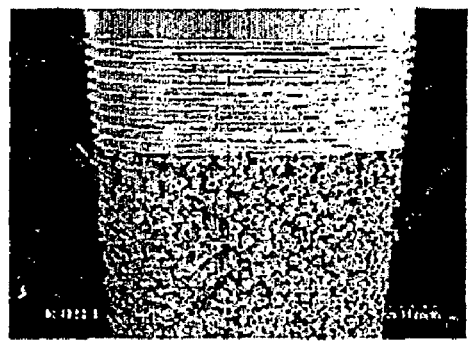
[Fig. 13a]
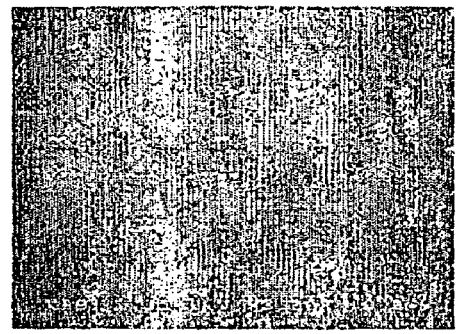
[Fig. 13b]
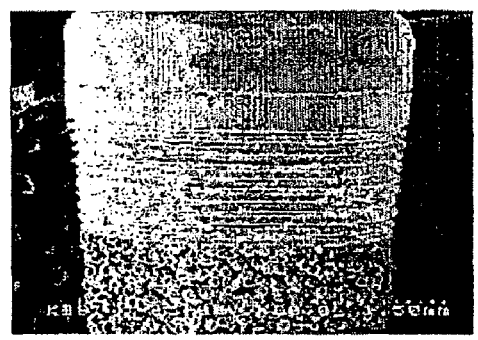
[Fig. 14a]
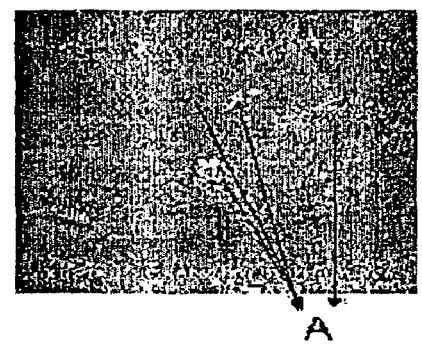
[Fig. 14b]

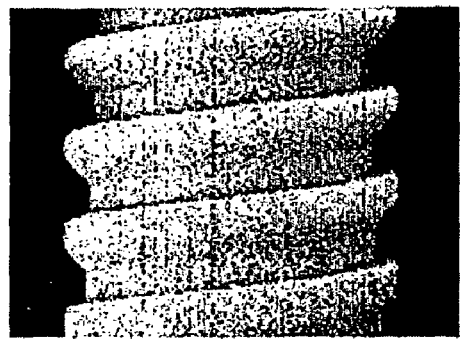
[Fig. 15a]
[Fig. 15b]
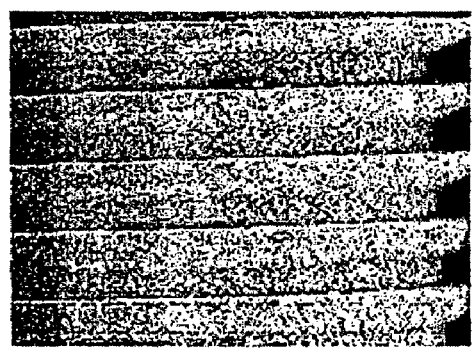
[Fig. 16a]
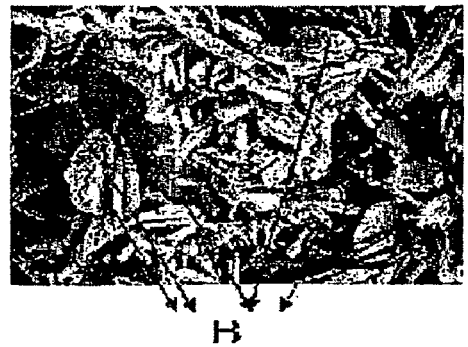
[Fig. 16b]

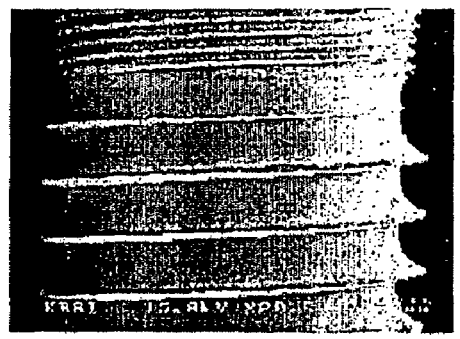
[Fig. 17a]
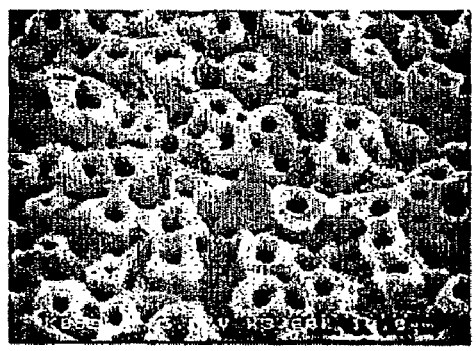
[Fig. 17b]
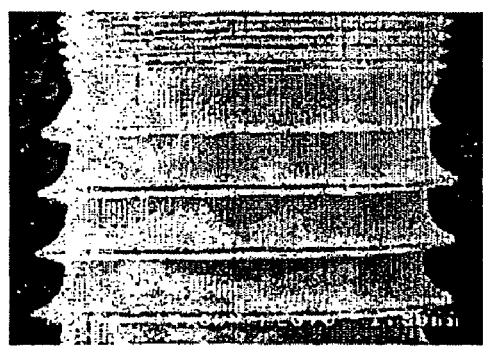
[Fig. 18a]
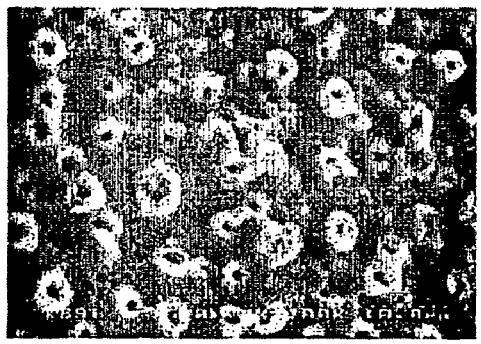
[Fig. 18b]

DENTAL IMPLANT COATED WITH RECOMBINANT BONE MORPHOGENIC PROTEIN

TECHNICAL FIELD

The present invention relates to a dental implant coated with recombinant bone morphogenic protein and a coating method thereof, and more particularly to a dental implant having a recombinant bone morphogenic protein coated on the processed surface thereof, which, when implanted into the jawbone, enables undifferentiated adult cells around the implant site to be rapidly differentiated into osteoblasts so as to induce osteoconductive healing to thereby reduce a healing period, as well as a coating method thereof.

BACKGROUND ART

When a general dental implant is implanted into the jawbone, osteoblasts derived from the surrounding bone tissue differentiate into new bone tissue in an osteoconductive and osteoinductive healing process. The new bone tissue adheres closely to the implant surface, so that the osseointegration of the implant with the surrounding bone tissue occurs to resist masticatory forces.

In the healing mechanism of prior implants, which have been used for implantation up to now, when bleeding occurs due to damage resulting from implant surgery, blood is filled into the space between the implant and a drill groove. When the filled blood comes into contact with the implant surface, a plasma protein layer is immediately adsorbed onto the implant surface, and platelets rapidly adhere to the adsorbed plasma protein layer and, at the same time, are activated. Various growth factors and cytokines are released from the activated platelets, and fibrin clots are rapidly formed due to various actions to clog the bleeding blood vessels, while cells of treating inflammations are collected in the wound sites. A series of such processes occur within about 72 hours after damage. The blood clots serve to stop the bleeding by blocking the broken blood vessels from an external environment and to store the released grown factors and acts to provide a temporary substrate for cell migration such that various cells required for bone formation or the treatment of inflammations can migrate to sites to be treated. Then, an angiogenesis process and a fibrous tissue formation process progress over about 4 weeks, while granulation tissue is formed and help undifferentiated cells to differentiate into osteoblasts. Then, the osteoblasts differentiate and develop into bone cells to form woven bone. The time required up to the formation of the woven bone is known to be about 2 months. In the characteristics of the woven bone, the formation of the woven tissue is a phenomenon that abnormally rapidly occurs due to a wound, the histological structure thereof is irregular compared to that of normal bone tissue, and thus the bone density thereof is also relatively low. After the woven bone is formed, the bone cells thereof are replaced with lamella bone having hard bone tissue. As the woven bone is completely replaced with the lamella bone, the implant is connected with the surrounding bone tissue, while the deposition of bone on the implant is completed and osseointegration between the implant and the bone tissue is completed through a bone remodeling process, so that the implant performs functions under normal forces. The time required for adaptation to the implant is 2-4 months depending on persons.

Also, in the current stage, the time for the bone tissue adhered to the interface with the implant to reach a level capable of mastication is 3-5 months for the lower jaw and 6-8 months for the upper jaw. This is because the osseointegration of the implant occurs only through an osteoconductive healing process. This process is called a healing period, in which bone cells naturally undergo a healing process in a normal human body. During this healing period, external stimuli such as inflammations or occlusal forces to the inserted implant should be limited such that the adhesion of bone tissue to the implant can be successively achieved. For this reason, a patient cannot masticate food for a long period of time and must continue to maintain oral hygiene performance to prevent infections. Thus, to reduce the bone healing period, technology for rapidly differentiating the surrounding undifferentiated adult cells into bone cells have been studied and developed in various ways.

As already found in several worldwide papers, recombinant human bone morphogenic proteins (BMPs) function to stimulate bone formation by moving adult stem cells from a site far away from the surrounding of the implant into the implanted site by chemotaxis so as to differentiate into osteoblasts. Methods of medical surgery using such recombinant bone morphogenic proteins (BMPs) are applied used in a wide range of fields, one of which is implant surgery.

DISCLOSURE OF INVENTION

Technical Problem

Meanwhile, as a patent relating to a growth-stimulating property imparted to the implant surface, Korean Patent Publication No. 2005-58452 (Published on 15 Jun., 2005) discloses an implant for implantation into either a bone tissue or a bone tissue supplemented with a bone substitute material. As disclosed in said patent, the surface of the implant, which comes into contact with bone tissue or grows around bone tissue or together with bone tissue, comprises a first-type region and a second-type region different from the first-type region, in which the first-type surface region is formed of compounds having the effects of bone integration, inflammation inhibition, infection treatment and growth stimulation effects so as to have a structure suitable for the growth of bone tissue. The first-type surface region is, for example, a biologically compatible surface made of, for example, titanium, and can be formed to have a structure suitable for the growth of bone tissue. Also, this surface can be additionally coated with a material containing calcium phosphate, can be modified with, for example, phosphate or peptide sequences and/or is made of a material, which can contain, for example a gel or polymer containing growth factors. For this reason, there are problems in that, in order to coat the growth-stimulating factors on the implant surface, the implant surface must be coated with either the calcium phosphate-containing material for fixing the growth-stimulation factors onto the implant surface or a fixture such as a gel or polymer containing the growth-stimulating factors.

Technical Solution

The present invention aims to develop a method for coating recombinant bone morphogenic proteins (BMPs) on the surface of an implant, such that the coated implant enables to undifferentiated adult cells around the surgical site of the implant to be rapidly differentiated into osteoblasts so as to induce osteoconductive healing to thereby reduce a healing period.

Accordingly, the present invention has been made to solve the above-described problems occurring in the prior art, and an object of the present invention is to provide a dental implant coated with recombinant bone morphogenic protein, which is obtained by coating the implant surface directly with recombinant bone morphogenic proteins by freeze drying in a negative-pressure atmosphere, without using a fixture for fixing the recombinant bone morphogenic proteins on the implant surface, and which, when the implant is implanted into the jawbone, enables undifferentiated adult cells around the implant site to be rapidly differentiated into osteoblasts so as to induce osteoconductive healing to thereby reduce a healing period, as well as a coating method thereof.

Another object of the present invention is to provide a dental implant coated with recombinant bone morphogenic protein, which does not employ any adhesive polymer for coating, and thus does not substantially cause a tissue inflammatory reaction for absorbing the polymer, as well as a coating method thereof.

Still another object of the present invention is to provide a dental implant coated with recombinant bone morphogenic protein, which is obtained by either embossing the implant surface with ceramic balls, or forming a sheet structure on the implant surface using calcium triphosphate or forming fine pores on the implant surface by anodic oxidation, and then coating recombinant bone morphogenic protein on the treated implant surface, such that the recombinant bone morphogenic protein is not easily detached from the implant surface during the surgical implantation of the implant, as well as a coating method thereof.

Yet another object of the present invention is to provide a dental implant coated with recombinant bone morphogenic protein, which has little or no side effects resulting from the bone morphogenic protein, because a minimum amount of the protein locally acts on tissue around the implant site, as well as a coating method thereof.

Still another further object of the present invention is to provide a dental implant coated with recombinant bone morphogenic protein, in which the bone morphogenic protein show pharmacological effects to enable undifferentiated adult cells around the implant to be differentiated into osteoblasts so as to induce enhanced osteoconductive healing, to thereby significantly reduce the osseointegration period of the implant, as well as a coating method thereof.

Advantageous Effects

As described above, according to the present invention, the implant surface having fine pores formed thereon is coated with the recombinant bone morphogenic protein by freeze drying in a negative-pressure atmosphere. Thus, because the coating film formed of the recombinant bone morphogenic protein is fixed to the fine pores formed on the implant surface, it is not peeled from the implant surface. Also, the implant does not employ any adhesive polymer for coating, and thus does not substantially cause a tissue inflammatory reaction for the absorption of the polymer.

Moreover, according to the present invention, recombinant bone morphogenic protein BMP-2 penetrates between the ceramic balls formed on the dental implant surface, the sheet structures of calcium triphosphate or the fine pores formed by anodic oxidation, so as to form a coating film. Thus, the recombinant bone morphogenic protein BMP-2 is not detached from the dental implant surface even during the surgical implantation of the implant. Also, because the recombinant bone morphogenic protein coated on the surface of the dental implant is coated mainly on the deep valley of the implant surface, it can be prevented from being peeled due to mechanical friction during the surgical implantation of the implant. Also, because a minimum amount of the protein coated on the implant surface locally acts on tissue around the implant site, the protein has little or no side effects. In addition, the protein shows pharmacological effects to enable undifferentiated adult cells around the implant to differentiate into osteoblasts so as to induce enhanced osteoconductive healing to thereby significantly reduce the osseointegration period of the implant.

BRIEF DESCRIPTION OF THE DRAWINGS

FIG. 1 is a cross-sectional view of a dental implant coated with recombinant bone morphogenic protein according to the prior art.

FIG. 2 is a 20-fold enlarged SEM photograph showing a state in which a recombinant bone morphogenic protein was coated on a dental implant surface using a method like the example of FIG. 1.

FIG. 3 is a 20-fold enlarged SEM photograph showing a state in which a recombinant bone morphogenic protein was coated on a dental implant surface using a method like the example of FIG. 1 in a manner different from the state of FIG. 2.

FIG. 4 is a perspective view of another implant coated with recombinant bone morphogenic protein according to the prior art.

FIG. 5 is a 2,000-fold enlarged SEM photograph showing a state in which fine pores having a size of 0.1-6□ were formed on a dental implant surface by anodic oxidation treatment according to the present invention.

FIG. 6 is a 2,000-fold enlarged SEM photograph showing a state in which fine pores having a size of 0.1-6□, which are different from those of FIG. 5, were formed on a dental implant surface by anodic oxidation treatment according to the present invention.

FIG. 7 is a 3,000-fold enlarged SEM photograph showing a state in which fine pores having a size of 0.1-6□ were formed on a dental implant surface by spark-anodic oxidation according to the present invention.

FIG. 8 is a 2,000-fold enlarged SEM photograph showing a state where the photograph of FIG. 7 was seen in inclined direction.

FIG. 9 is a 2,000-fold enlarged SEM photograph showing a state in which an unsaturated protein solution was coated on a dental implant surface according to the present invention and, as a result, the protein solution was encapsulated into less than 1□ of fine pores distributed on the valley of the surface.

FIG. 10 is 2,000-fold enlarged SEM photograph showing a state in which a saturated protein solution was coated on a dental implant surface according to the present invention and, as a result, a surplus of the protein mass was bound to the protein film coated on less than 1□ of fine pores.

FIG. 11 is a photograph showing a 0.5-ml polypropylene tube.

FIG. 12 is a photograph showing a 1.5-ml polypropylene tube.

FIG. 13a is a 20-fold enlarged SEM photograph showing the state of a dental implant surface before coating the implant surface with ceramic balls.

FIG. 13b is a 3,000-fold enlarged SEM photograph showing a dental implant surface before its coating with ceramic balls, but after its coating with a recombinant bone morphogenic protein solution.

FIG. 14a is a 20-fold enlarged SEM photograph showing the surface of a dental implant surface coated with ceramic balls.

FIG. 14b is a 3,000-fold enlarged SEM photograph showing the state of a ceramic ball-coated dental implant surface after coating a recombinant bone morphogenic protein on the surface.

FIG. 15a is a 20-fold enlarged SEM photograph showing the state of a dental implant surface before its coating with calcium triphosphate.

FIG. 15b is a 3,000-fold enlarged SEM photograph showing the state of a dental implant surface before its coating with calcium triphosphate, but after its coating with recombinant bone morphogenic protein.

FIG. 16a is a 20-fold enlarged SEM photograph showing the state of a dental implant surface coated with calcium triphosphate.

FIG. 16b is a 3,000-fold enlarged photograph of a calcium triphosphate-coated dental implant surface after coating a recombinant bone morphogenic protein on the surface.

FIG. 17a is a 20-fold enlarged SEM photograph showing the state of a dental implant surface before anodic oxidation treatment.

FIG. 17b is a 3,000-fold enlarged SEM photograph showing the state of a dental implant surface before anodic oxidation treatment, but after coating a recombinant bone morphogenic protein on the surface.

FIG. 18a is a 20-fold enlarged SEM photograph showing the state of a dental implant surface after anodic oxidation treatment.

FIG. 18b is a 3,000-fold enlarged SEM photograph showing the state of an anodic oxidized dental implant surface after coating a recombinant bone morphogenic protein on the surface.

BEST MODE FOR CARRYING OUT THE INVENTION

A method for coating a recombinant bone morphogenic protein on the surface of a dental implant comprises:

i) a pretreatment step of processing the surface of the implant (implant surface-processing step);

ii) a step of preparing a recombinant bone morphogenic protein solution by adding 4 mg of recombinant bone morphogenic protein to 1 ml of acidic buffer solution (BMP solution preparation step);

iii) placing 60□ of the BMP solution of said step ii) in a 0.5-ml volume polypropylene tube and immersing in the polypropylene tube the implant having fine pores formed on the surface thereof (implant immersion step);

iv) placing the polypropylene tube having the implant immersed therein in a 1.5-ml volume polypropylene tube, sealing the 1.5-ml volume tube, and freezing the 1.5-ml volume tube in a freezer at −75±0.5° C. for 3-4 hours (first freezing step);

v) opening the lid of the 1.5-ml volume polypropylene tube frozen in the freezer, and drying the 1.5-ml volume tube in a freeze dryer pre-cooled to 75±5° C. for 8 hours (second freeze-drying step). Through the above steps, the recombinant bone morphogenic protein is coated on the surface of the implant.

The second freeze-drying step is followed by a step of packaging the polypropylene tube in an aseptic environment and storing the packaged tube at room temperature or in a refrigerator in a dehumidified atmosphere (storage step).

The surface of the implant used in said step i) can be selected from the group consisting of an implant surface having a surface shape modified with a titanium oxide layer; an implant surface coated with titanium balls or ceramic balls, and an implant surface coated with calcium triphosphate. In addition, dental implants having surfaces treated by other general methods can also be used in said step i).

Said implant having a surface shape modified with a titanium oxide layer is obtained by coating titanium on an implant surface subjected to electro-chemical treatment, mechanical sandblasting or chemical acid corrosion.

Said electro-chemical treatment (anodic oxidation coating) is carried out in the following manner. To 1 liter of 0.5 M mixture solution prepared by mixing 95% sulfuric acid solution with 85% phosphoric acid solution at a weight ratio of 5:1, 2 ml of 2% hydrogen peroxide to prepare an electrolyte solution. The electrolyte solution is placed in an electrolytic bath, in which a cathode and an anode are electrically connected with a titanium rod and the implant, respectively. Then, the implant is subjected to anodic oxidation treatment by applying constant current in conditions of current density of 1-10 $A/dm^2$ and voltage of 150-250 V. As the current density is lowered to 1 $A/dm^2$, the formation of an oxide coating layer on the implant surface is completed. As shown in SEM photographs in FIGS. 5 and 6, this oxide coating film formed on the implant surface has 0.1-6□ of fine pores formed therein. In the above anodic oxidation treatment, the distance between the cathode and the anode is set at 5 cm, and the temperature of the electrolyte solution is 20° C.

The fine pores formed on the implant surface by the above spark-anodic oxidation process are shown in detail in a photograph in FIG. 7. As can be seen in the photograph of FIG. 7, the fine pores having a size of 0.1-6□ are formed on the implant surface as a result of the spark-anodic oxidation. FIG. 8 shows the observation of the fine pores of FIG. 7 in an inclined direction. As shown in FIG. 8, fine pores having a size of more than 1□ have a crater higher than that of the surrounding fine pores, whereas fine pores having a size of less than 1□ are distributed in deep valleys between great craters.

Also, said implant having a surface coated with titanium balls or ceramic balls is prepared in the following manner. First, an implant body is prepared by mechanical cutting, and then the surface of the implant body is coated with titanium balls or ceramic balls by a high-temperature spraying process using a plasma spray such that it can show a roughness of about 15□.

In said step the recombinant bone morphogenic protein solution is prepared by adding 4 mg of recombinant bone morphogenic protein to 1 ml of acidic buffer solution. As used herein, the term "acidic buffer solution" refers to a MES (2-{N-morpholino} ethanesulfonic acid) buffer solution having an acidity of 5.0. If the amount of the recombinant bone morphogenic protein, which is added to the acidic buffer solution, is less than 4 mg, the effect of the BMP protein can be reduced, because the amount of the coated BMP is too low. The recombinant bone morphogenetic protein used herein is preferably a BMP-2 in terms of functions.

In said step iii), the implant having the fine pores formed thereon is immersed in the recombinant bone morphogenic protein solution prepared in said step such that the recombinant bone morphogenic solution can be coated in the fine pores.

The process, in which the recombinant bone morphogenic protein solution is coated in the fine pores, is shown in a photograph in FIG. 9. As shown in the photograph of FIG. 9, as a result of coating the protein solution on the implant surface, the protein solution is first encapsulated into less than 1□ of fine pores distributed at the valley of the surface. Then, as shown in a photograph in FIG. 10, a surplus of the protein in the form of a mass is bound to the protein film coated in the fine pores having a size of less than 1□.

The 0.5-ml volume polypropylene tube, which is used in said step is shown in FIG. 11. The term 1.5-ml volume polypropylene tube as shown in FIG. 12 refers to a tube having a volume greater than that of the 0.5-ml volume polypropylene tube.

In said step iv), the 1.5-ml volume polypropylene tube containing the coated implant is frozen in a freezer at a temperature of −75 0.5° C. for 3-4 hours, such that the recombinant bone morphogenic protein coated in the fine pores can be fixed to the fine pores.

Said step v) is carried out to evaporate water from the recombinant bone morphogenic protein coated in the fine pores as shown in the photograph of FIG. 5 or 6. This step is preferably performed by opening the lid of the 1.5-ml volume polypropylene tube frozen in the freezer, placing the opened tube in a freeze dryer precooled to 75 5° C., and freeze-drying the tube in the freeze dryer at a pressure of 0.05 0.005 torr for 8 hours. FIG. 5 is a 2,000-fold enlarged SEM photograph showing a state in which fine pores having a size of 0.1-6□ were formed on the implant surface by spark-anodic oxidation treatment according to the present invention. FIG. 6 is a 2,000-fold enlarged SEM photograph showing a state in which fine pores having a size of 0.1-6□, different from those of FIG. 5, were formed on the implant surface by sparkanodic oxidation treatment according to the present invention.

Hereinafter, the present invention will be described in further detail with reference to examples. It is to be understood, however, that these examples are not to be construed to limit the scope of the present invention.

1. Preparation of dental implant samples

The following dental implant samples were prepared: a dental implant sample coated with ceramic balls (sample 1; FIG. 14*a*); a dental implant sample coated with calcium triphosphate (sample 2; FIG. 16*a*); and a dental implant sample subjected to anodic oxidation (sample 3; FIG. 18*a*). Also, as samples for comparison with said samples 1 to 3, the following dental implant samples were prepared: a dental implant sample before being coated with ceramic balls (sample 4; FIG. 13*a*); a dental implant sample before coating with calcium triphosphate (sample 5; FIG. 15*a*); and a dental implant sample before being subjected to anodic oxidation treatment (sample 6; FIG. 17*b*).

2. Coating with recombinant bone morphogenic protein

Each of said samples 1 to 6 was coated with recombinant bone morphogenic protein BMP-2 according to the following conditions. Specifically, in Examples 1 to 3, the recombinant bone morphogenic protein was coated on the surface of each of the dental implant samples 1 to 3, and in Comparative Examples 1 to 3, the recombinant bone morphogenic protein was coated on the surface of each of the dental implant samples 4 to 6.

The coating of each sample with the recombinant bone morphogenic protein was performed in the following manner.

To 1 ml of an acidic buffer solution, 4 mg of the recombinant bone morphogenic protein BMP-2 was added, thus preparing a recombinant bone morphogenic protein solution. 60□ of the prepared protein solution was added into each of six 0.5-ml volume polypropylene tubes, and said samples were immersed in the tubes, respectively.

Then, the 0.5-ml volume polypropylene tubes each having the implant immersed therein were placed in six 1.5-ml volume polypropylene tubes, respectively, sealed and then frozen in a freezer at −75±0.5° C. for 3 hours. Then, the lid of each of the frozen 1.5-ml volume polypropylene tubes was opened and the opened tubes were placed in a freeze dryer pre-cooled to a temperature of −75±5° C., in which the tubes were freeze-dried at a pressure of 0.05±0.005 torr for 8 hours. Then, the lids of the tubes were immediately closed, and the tubes were stored in a refrigerator to prevent contamination and moisture absorption.

3. Coated and adhered state of recombinant bone morphogenic protein

The surface of each of the dental implant samples according to Examples 1 to 3 and Comparative Examples 1 to 3 was observed for the state of the fine pores formed thereon and the coated and adhered state of the recombinant bone morphogenic protein through a scanning electron microscope (SEM). The observation results are shown in Table 1 below.

TABLE 1

| | Examples | | | Comparative Examples | | |
|---|---|---|---|---|---|---|
| | 1 (sample 1) | 2 (sample 2) | 3 (sample 3) | 1 (sample 4) | 2 (sample 5) | 3 (sample 6) |
| Coated state of recombinant bone morphogenic protein | FIG. 14b | FIG. 16b | FIG. 18b | FIG. 13b | FIG. 15b | FIG. 17b |

The observation results for the coating films coated on the surfaces of the dental implants coated with ceramic balls and the coating films coated on the surfaces of the dental implants uncoated with ceramic balls are as follows. In the of Comparative Example 1, as shown in FIG. 13*b*, the recombinant bone morphogenic protein was coated on the even surface of the dental implant, suggesting that the recombinant bone morphogenic protein BMP-2 was attached in a state where it can be easily detached during the implantation of the dental implant. On the other hand, in the case of Example 1 as shown in FIG. 14*b*, the recombinant bone morphogenic protein was coated on the ceramic ball-coated dental implant surface in the form of a mass or a uniform coating film, and particularly, as shown as A in FIG. 14*b*, the recombinant bone morphogenic protein was penetrated and impregnated between the ceramic balls, suggesting that the recombinant bone morphogenic protein BMP-2 was attached in a state where it cannot be easily detached even during the implantation of the dental implant.

Also in the case of Comparative Example 2, as shown in FIG. 15*b*, the recombinant bone morphogenic protein was coated on the even surface of the dental implant in the form of a thin coating film, suggesting that the recombinant bone morphogenic protein BMP-2 was attached in a state where it can be easily detached during the implantation of the dental implant. On the other hand, in the case of Example 2, as shown in FIG. 16b, calcium triphosphate was coated on the surface of the dental implant to have sheet structures as shown as B in the figure, and the recombinant bone morphogenic protein was penetrated and impregnated between the sheet structures of calcium triphosphate, suggesting that the recombinant bone morphogenic protein BMP-2 was attached in a state where it cannot be easily detached even during the implantation of the dental implant.

In the case of Comparative Example 3, as shown in FIG. 17b, the recombinant bone morphogenic protein was coated on the surface of the dental implant in the form of a thin coating film, suggesting that the recombinant bone morphogenic protein BMP-2 was attached in a state where it can be easily detached during the implantation of the dental implant. On the other hand, in the case of Example 3, as shown in FIG. 18b, the recombinant bone morphogenic protein was penetrated between the fine pores in the anodic oxidized coating film formed on the surface of the dental implant at high protein concentration, suggesting that the recombinant bone morphogenic protein BMP-2 was attached in a state where it cannot be easily detached even during the implantation of the dental implant.

As can be seen from the results shown in Table 1 above, in Comparative Examples 1 to 3, the recombinant bone morphogenic protein BMP-2 was detached to the dental implant surface in a state where it can be easily detached during the implantation of the dental implant. On the other hand, in Examples 1 to 3, the recombinant bone morphogenic protein BMP-2 was penetrated between the ceramic balls or calcium triphosphate sheet structures coated on the dental implant surface or between the fine pores formed by anodic oxidation, so as to form a coating film of the protein, suggesting that the recombinant bone morphogenic protein BMP-2 was attached in a state where it cannot be easily detached even during the implantation of the dental implant.

Although the inventive dental implant coated with the recombinant bone morphogenic protein, and the method for coating the protein on the implant surface, have been described in detail with reference to above Examples, those skilled in the art will appreciate that the scope of the present invention should not be limited only by above Examples, and various modifications, additions and substitutions are possible, without departing from the scope and spirit of the invention as disclosed in the accompanying claims.

MODE FOR THE INVENTION

The present invention provides a dental implant coated with recombinant bone morphogenic protein, which is obtained by processing the surface of a dental implant, coating the processed surface with a solution containing recombinant bone morphogenic protein molecules, and freeze-drying the coated implant in a negative-pressure atmosphere.

In the present invention, the implant to be coated with recombinant bone morphogenic protein on the surface thereof may be any implant treated according to a suitable surface treatment method. Typically, the implant to be coated with recombinant bone morphogenic protein can be selected from the group consisting of an implant having a surface modified with a titanium oxide layer, an implant having a surface coated with titanium balls or ceramic balls, and an implant having a surface coated with calcium triphosphate. In addition, implants having surfaces treated by other general methods can also be used.

As used herein, the phrase "implant having a surface modified with a titanium oxide layer" refers to an implant having a surface subjected to electro-chemical treatment, mechanical sandblasting treatment, or chemical acid corrosion treatment so as to increase the surface area of the implant. Also, the phrase "implant having a surface coated with titanium balls or ceramic balls" refers to an implant having an increased surface area achieved by attaching microscopic-size grains made of titanium or ceramic material to the implant surface at high temperature.

In the case of the implant having a surface shape modified with a titanium oxide layer by electro-chemical treatment, current density and voltage magnitude in treating the implant surface by spark-anodic oxidation are preferably 1-10 A/dm$^2$ and 150-250 V, respectively. At a current density of 1-10 A/dm$^2$, the voltage in the anodic oxidation treatment increased with the passage of time in a constant current condition so as to generate sparks, and at a voltage of about 240 V, the current density in the anodic oxidation treatment was maintained at a substantially constant level. This is believed to be because the sparks occurred due to dielectric breakdown at the surface of the barrier layer, so that the growth of the coating film was very slow or was not increased. Thus, the surface pattern of the formed oxide coating film varies with a change in the current density. Regarding the growth process of the anodic oxidized coating film, it is known that a very compact oxide coating layer is initially formed on the surface of the metal, and this layer becomes a barrier layer interfering with the flow of electric current with the passage of time, and then continues to grow with an increase in voltage while forming a porous surface layer. After the compact oxide coating layer is formed, the initial coating layer is broken by spark discharge and, at the same time, restored, while the initial oxide coating layer is locally heated to dissolve the surface of the coating layer. As a result, innumerable pores, which can be regarded as traces of the spark discharge, are created out of the barrier layer, while the total thickness of the coating layer increases. At this time, anions in the electrolyte are incorporated into the coating layer by an electric field. If the magnitude of voltage is less than 150 V, the surface of the implant will not be sufficiently anodic-oxidized, so that the thickness of the oxide coating layer becomes too small, and thus, fine pores will not be sufficiently formed on the implant surface. On the other hand, if the magnitude of voltage exceeds 250 V, the surface of the implant will be excessively oxidized, so that the thickness of the oxide coating layer becomes too large, while the implant surface becomes too rough without the formation of fine pores.

Another implant, which can be used in the present invention, is the implant coated with titanium balls or ceramic balls. The implant coated with titanium balls is obtained by preparing an implant body by mechanical cutting, and coating dissolved titanium to the surface of the implant body with a plasma spray using a high-temperature spraying process. It is known that this implant surface shows a roughness of about 15☐ and can strongly resist rotatory powder, and osteoblasts well adhere to this implant surface. Also, this implant surface is larger in surface area than a machined surface, and thus is relatively advantageous. In addition, in an implant having a machined surface, the length thereof is emphasized, whereas, in the implant having a titanium plasma sprayed surface (TPS), the diameter thereof is of more importance than the length thereof.

The recombinant bone morphogenic protein, which is coated on the implant having the above-described surface, is preferably BMP-2. The recombinant bone morphogenic protein BMP-2, which is used in the present invention, is a homodimer made of a combination of two peptide molecules each consisting of 114 amino acids shown in Table 2 below.

TABLE 2

Amino acid sequence of polypeptide constituting BMP-2

QAKHKQRKRLKSSCKRHPLYVDFSDVGWNDWIVAPPGYHAFYCHGECPFP

LADHLNSTNHAIVQTLVNSVNSKLPKACCVPTELSAISMLYLDENEKVVL

KNYQDMVVEGCGCR

The alphabets listed in Table 2 above have the following meanings: A: alanine; R: arginine; N: asparagines; C: cystein; Q: glutamine; E: glutamic acid; G: glycine; H: histidine; I: isoleucine; L: leucine; K: lysine; M: methionine; F: phenylalanine; P: praline; S: serine; T: threonine; W: tryptophane; Y: tyrosine; and V: valine.

The protein BMP-2, which is used in the present invention, is made in osteoblasts and released to the extracellular substrate, in which it stimulates itself and the surrounding cells to form bone. In an animal test, when BMP-2 is purified and grafted into parts other than bone, it can be seen that the BMP-2 protein stimulates the surrounding cells to form bone, so that new bone tissue is formed at the grafted parts. The BMP protein binds to a BMP receptor in the membrane of susceptible cells to act as a system of transferring a signal into the cells by extracellular stimulation. As reported in various studies, the BMP-2 protein dominates in the ability to differentiate cells into bone cells, compared to a property to grow cells.

The action mechanism of BMP-2 in cells will now be briefly described. When BMP binds to BMP receptor (BMPR-II and BMPR-I) proteins in the cell membrane, signaling proteins Smad1, Smad5 and Smad8 are phosphorylated to form a complex with Smad4. This complex moves into the nucleus and activates a transcription regulator such as RunX2. The activated transcription regulator activates various genes associated with bone formation so as to initiate bone formation. The bone-inducing ability of BMP-2 was already demonstrated in preclinical models and evaluated in clinical trials. In some cases, the effect of BMP-2 on osseointegration is also shown to be superior to the effect of an autogenous bone graft.

The action of rhBMP-2 (recombinant human bone morphogenic protein-2) in an implant healing process using the recombinant bone morphogenic protein BMP-2, which is used in the present invention, will now be described. During a process of healing after bleeding resulting from injury caused by implant surgery, rhBMP-2 directly acts on a process in which undifferentiated cells differentiate into osteoblasts, which are then collected together to form bone. At this time, rhBMP-2 acts as a key protein. Because BMP is a protein produced in human beings, it is made in human beings in a necessary amount in case of need, even if it is not administered from an external source. During the above-described process, BMP is normally formed by cells in a woven bone formation process and secreted to stimulate itself and the surrounding cells to promote bone formation. However, because cells must receive a signal in order to produce any protein, steps of making that signal sequentially occur. Thus, the provision of rhBMP-2 from an external source results in the effect of reducing previous steps. In a process in which a wound of bone tissue is healed, woven bone occurs to induce subsequent processes and then disappears, and these induction and disappearance processes are repeated such that hard bone tissue is formed. Therefore, according to the present invention, rhBMP-2, which induces hard bone tissue, is administered from an external source, and thus a healing period can be reduced. In other words, the woven bone-forming step is entered before completion of the formation of granulation tissue, which occurs over about 2 months, and also a period for transition from woven bone into lamella bone is reduced. Thus, the surgical implantation of the implant coated with rhBMP-2 has a disadvantage in that healing can be can be achieved within a short period (less than 2 weeks) without considering the time required for general implants to be stabilized.

The rhBMP-2 protein, which is used in the present invention, is coated on the implant surface using a freeze-drying technique. When the implant is inserted into a wound site, the implant surface will be surrounded by blood clots. If the rhBMP-2 protein on the implant surface is present in a liquid phase, it has a high likelihood to be easily washed out before formation of blood clots even with a trace amount of blood or body fluid. However, according to the present invention, this risk can be reduced, because rhBMP-2 is coated on the implant surface by freeze-drying. Also, because rhBMP-2 is stored in blood clots while it can be prevented from being rapidly released, it induces bone cells and blood vessel cells at local sites, and thus an early healing mechanism is entered. Also, as described above, the initial healing process is reduced, so that the osseointegration of the implant is just performed due to the proliferation of bone cells and blood vessel cells.

Moreover, the freeze-drying process in the present invention consists of a first freezing step, followed by a second freeze-drying step. The first freezing step is preferably carried out in a freezer at −75±0.5° C. or higher for 3-4 hours. If the freezing temperature is higher than −74.5° C. or the freezing time is shorter than 3 hours, sufficient freezing cannot be achieved, so that, when vacuum is applied in the second freeze-drying step, the protein solution can be lost. On the other hand, the freezing temperature is lower than 75.5° C. or the freezing time exceeds 4 hours, sufficient freezing will be ensured, but any increased freezing effect resulting from the lowering of the freezing temperature or the increase in the freezing time will not be obtained.

Also, the second freeze-drying step is preferably carried out by placing the sample in a freezing dryer pre-cooled to 75±5° C. and freeze-drying the sample at a pressure of 0.05±0.005 ton for 8 hours. These temperature and pressure range conditions are the most preferred conditions where the sample can be sufficiently dried within 8 hours. If the freeze drying time in said temperature and pressure range conditions is less than 8 hours, complete drying will not be achieved due to the insufficient evaporation of water, and thus, when the implant is exposed to room temperature, the protein will be present as a solution due to the remaining water, so as to increase the risk of the lose and contamination of the protein. On the other hand, the freezing time in said temperature and pressure conditions exceeds 8 hours, sufficient drying will be achieved, but any increased freezing effect resulting from the increase in the freezing time will not be obtained.

INDUSTRIAL APPLICABILITY

As described above, the present invention provides the dental implant coated with recombinant bone morphogenic protein and the method for coating the protein on the dental implant. More particularly, the present invention provides the dental implant having recombinant bone morphogenic protein coated on the processed surface thereof, which, when implanted into the jawbone, enables undifferentiated adult cells around the implant site to rapidly differentiate into osteoblasts so as to induce osteoconductive healing to thereby reduce a healing period, as well as a coating method thereof.

The invention claimed is:

1. A method for coating a recombinant bone morphogenic protein on the surface of a dental implant, comprising:
   i) a pretreatment step of coating the surface of the implant with titanium oxide, titanium balls, ceramic balls or calcium triphosphate, or increasing the surface area of the implant by processing the implant surface by mechanical sandblasting treatment or chemical acid corrosion treatment;
   ii) a step of the coating the pretreated implant with a recombinant bone morphogenic protein wherein the bone morphogenic protein is rhBMP-2;
   iii) freezing the BMP2-coated implant in a freezer at $-75\pm0.5°$ C. for 3-4 hours (first freezing step); and
   iv) freeze-drying the implant of Step iii) in a freeze dryer pre-cooled to $-75\pm0.5°$ C. at a pressure of 0.05-0.005 torr for 8 hours (second freeze-drying step).

2. The method of claim 1, wherein the rhBMP-2 is a homodimer, each polypeptide consisting of 114 amino acids as defined by SEQ ID NO: 1.

* * * * *

SEQUENCE LISTING

<160> NUMBER OF SEQ ID NOS: 1

<210> SEQ ID NO 1
<211> LENGTH: 114
<212> TYPE: PRT
<213> ORGANISM: Artificial Sequence
<220> FEATURE:
<223> OTHER INFORMATION: Synthetic Construct

<400> SEQUENCE: 1

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Leu Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```